United States Patent

Mahler et al.

[11] Patent Number: 5,830,325
[45] Date of Patent: Nov. 3, 1998

[54] SEPARATING AND REMOVING 1, 1, 1-TRIFLUOROETHANE BY USING AZEOTROPIC DISTILLATION

[75] Inventors: Barry Asher Mahler, Glen Mills, Pa.; Ralph Newton Miller, Newark, Del.

[73] Assignee: E. I. du Pont de Nemours and Company, Wilmington, Del.

[21] Appl. No.: 625,579

[22] Filed: Mar. 28, 1996

Related U.S. Application Data

[63] Continuation of Ser. No. 382,115, Feb. 1, 1995, abandoned.

[51] Int. Cl.$^6$ .................................................. B01D 3/36
[52] U.S. Cl. .............................. 206/56; 570/178; 203/43; 203/55; 203/63; 203/64; 203/65; 203/66; 203/71; 203/73; 203/80
[58] Field of Search ................................ 203/43, 55, 56, 203/63, 64, 65, 66, 71, 73, 80; 250/171; 570/178

[56] References Cited

U.S. PATENT DOCUMENTS

| | | | |
|---|---|---|---|
| 3,282,801 | 11/1966 | Wiist | 203/63 |
| 3,732,150 | 5/1973 | Bailey | 203/44 |
| 3,819,493 | 6/1974 | Fozzard et al. | 570/178 |
| 4,973,774 | 11/1990 | Rozen et al. | 570/178 |
| 4,996,379 | 2/1991 | Oshio | 570/176 |
| 5,049,241 | 9/1991 | Leverett et al. | 570/178 |
| 5,087,329 | 2/1992 | Felix | 570/178 |
| 5,200,431 | 4/1993 | Dattani et al. | 570/178 |
| 5,211,867 | 5/1993 | Shankland | 252/67 |
| 5,421,964 | 6/1995 | Mahler et al. | 570/178 |

FOREIGN PATENT DOCUMENTS

| | | | |
|---|---|---|---|
| 526 745 A1 | 2/1993 | European Pat. Off. | C09K 5/04 |
| 574756 | 12/1993 | European Pat. Off. | 570/178 |
| 598 907 A1 | 6/1994 | European Pat. Off. | C09K 5/04 |
| 0 626 362 A1 | 11/1994 | European Pat. Off. . | |
| WO 96/23752 | 8/1996 | European Pat. Off. . | |
| 1 578 933 | 12/1980 | United Kingdom | C07C 19/08 |
| WO 94/00528 | 1/1994 | WIPO | C09K 5/04 |
| WO94/04628 | 3/1994 | WIPO . | |

*Primary Examiner*—Timothy McMahon

[57] ABSTRACT

The disclosure relates to separating 1,1,1-trifluoroethane (HFC-143a from fluorocarbon impurities by using extractive distillation with an extractive agent comprising an alcohol. Examples of suitable extractive agents comprise at least one member from the group of methanol, butanol, ethanol, propanol, their isomers and cyclic compounds thereof, among others.

5 Claims, 5 Drawing Sheets

SEPARATING AND REMOVING 1, 1, 1-TRIFLUOROETHANE BY USING AZEOTROPIC DISTILLATION

This is a continuation of application Ser. No. 08/382,115 filed Feb. 1, 1995, now abandoned.

FIELD OF THE INVENTION

The instant invention relates to the field of removing fluorocarbon impurities from 1,1,1-trifluoroethane (HFC-143a) and 1,1,1-trifluoroethane containing mixtures by using an extractive distillation process that employs alcohols.

BACKGROUND OF THE INVENTION

New regulations have been designed to protect the stratospheric ozone layer from possible damage by fully halogenated chlorofluorocarbons. 1,1,1-trifluoroethane ($CF_3CH_3$ or HFC-143a) is useful either alone or in blends with other compounds as a refrigerant, blowing agent, cleaning agent, an aerosol propellant, heat transfer medium, fire extinguishing agent, power cycle working fluid, polymerization medium, particulate removal fluid, carrier fluids, buffing abrasive agent, displacement drying agent, among many other applications.

1,1,1-trifluoroethane is typically made by processes well known in the art, such as by fluorination and/or hydrogenolysis of various two-carbon chlorocarbons or chlorofluorocarbons.

Various fluorocarbon co-products and by-products may be present in 1,1,1-trifluoroethane as an impurity. After distillation to remove the bulk of impurities including any hydrogen chloride, hydrogen fluoride and/or easily separable fluorocarbons, the remaining fluorocarbon impurities typically include chloropentafluoroethane (CFC-115), pentafluoroethane (HFC-125), dichlorodifluoromethane (CFC-12), chlorodifluoromethane (HCFC-22), difluoromethane (HFC-32), chlorotrifluoroethylene (HCFC-1113), 1,1,2-trifluoroethane (HFC-143), 2-chloro-1,1,1-trifluoroethane (HCFC-133a), 1,1,1,2-tetrafluoroethane (HFC-134a), 1-chloro-1,1-difluoroethane (HCFC-142b), 1,1-difluoroethane (HFC-152a), ethane, among other compounds.

The presence of even relatively small amounts of these various impurities in the trifluoroethane product may be undesirable in many applications of these products. While certain impurities in the trifluoroethane product can be readily removed by conventional distillation, small amounts of certain other close-boiling impurities are difficult, if not impossible, to remove by conventional distillation. There is a need for a purification process which will remove several of these close-boiling impurities from trifluoroethane.

Whenever an extractive distillation process is employed for separating certain compounds, it is necessary to discover an extractive agent which will be effective to sufficiently enhance the desired separation process.

U.S. Pat. No. 3,732,150 (Phillips Petroleum, 1971) discloses a process for separating HFC-125 from a mixture with HFC-143a by using NH3.

European Patent 526,745 (Daikin, 1993), and U.S. Pat. No. 5,211,867 (Allied-Signal, 1993) each disclose various azeotropic compositions of HFC-143a and HFC-125 useful for refrigeration and other applications.

World Patent 9,306,186 (Daikin, 1993) discloses a binary mixture of 5–95 mole % HFC-143a and 95–5 mole % HFC-32 useful for refrigeration and for other applications.

The entire disclosure of each of the above-identified patent documents is hereby incorporated by reference.

CROSS-REFERENCE TO RELATED PATENTS AND PATENT APPLICATIONS

This invention is related to U.S. patent application Ser. No. 07/905,424 (corresponding to World Patent Publication No. 94/00528), and U.S. patent application Ser. No. 08/192, 664, filed on Feb. 7, 1994, and Ser. No. 08/378,349 (DuPont Docket No. CH-2408-A) filed on even date herewith. The disclosure of each of the cross-referenced documents is hereby incorporated by reference.

SUMMARY OF THE INVENTION

Fluorination or hydrogenolysis can be employed for manufacturing a trifluoroethane product, i.e., HFC-143a. For example, a process for manufacturing HFC-143a by hydrodehalogenating CFC-114a is disclosed in Great Britain Patent No. 1,578,933 and U.S. Pat. No. 4,996,379; the disclosures of which are hereby incorporated by reference.

The HFC-143a product may contain a variety of fluorocarbon co-products, such as chloropentafluoroethane (CFC-115), pentafluoroethane (HFC-125), dichlorodifluoromethane (CFC-12), chlorodifluoroethane (HCFC-22), difluoromethane (HFC-32), chlorotrifluoroethylene (HCFC-1113), 1,1,2-trifluoroethane (HFC-143), 2-chloro-1,1,1-trifluoroethane (HCFC-133a), 1,1,1,2-tetrafluoroethane (HFC-134a), 1-chloro-1,1-difluoroethane (HCFC-142b), 1,1-difluoroethane (HFC-152a), ethane, among other impurities. The presence of even relatively small amounts of such impurities in the HFC-143a product is undesirable in many applications. While the invention is capable of processing a wide range of products, typically the HFC-143a product will contain less than about 25 wt. % impurities. Chlorofluorocarbon impurities such as chloropentafluoroethane (CFC-115) and dichlorodifluoromethane (CFC-12) are considered environmentally harmful and are being regulated out of the marketplace. Hydrochlorofluorocarbons (HCFCs) are also facing regulations because of possible environmental effects. While some of these impurities in the HFC-143a product can be readily removed by conventional distillation, small amounts of certain other close-boiling impurities are difficult, if not impossible, to remove by using conventional methods. In particular, CFC-115, HFC-125, CFC-12, HFC-32, HCFC-22 and ethane are difficult to separate from the HFC-143a by using conventional distillation.

HFC-125 can form an azeotropic or azeotrope-like composition with HFC-143a. In addition, we have found that CFC-115 and HFC-32 will each also form azeotropic or azeotrope-like compositions with HFC-143a under certain conditions. The formation of such azeotropes makes complete separation of these compounds from HFC-143a by using conventional distillation difficult or impossible.

CFC-12 and HFC-143a can form a vapor-liquid equilibrium pinchpoint as a concentration of 100% HFC-143a is approached, thereby making removing low concentrations of CFC-12 difficult and expensive, e.g., by requiring relatively large distillation columns. HCFC-22 and ethane can each similarly form vapor-liquid equilibrium pinchpoints with HFC-143a such that removing trace levels of HCFC-22 and/or ethane from HFC-143a is difficult and expensive. By "pinch-point" it is meant that the relative volatility of the components of the mixture approaches 1.0.

Other fluorocarbons such as 1,1,2-trifluoroethane (HFC-143), 2-chloro-1,1,1-trifluoroethane (HCFC-133a), chlorotrifluoroethylene (HCFC-1113), 1,1,1,2-tetrafluoroethane (HFC-134a), 1-chloro-1,1-difluoroethane (HCFC-142b), 1,1-difluoroethane (HFC-152a), among others, can be separated from HFC-143a by using conventional distillation. However, removing combinations of such impurities from HFC-143a would require additional processing costs due to the multitude of purification steps required.

An alternate method of separating specific components in a mixture is by extractive distillation. Extractive distillation is employed when the components of the mixture may have differing volatilities, but such a difference is insufficient to permit effective separation of the components by using conventional distillation. In extractive distillation, an extractive agent is added that causes the difference in volatilities of the components in the starting mixture to become amplified such that the relative volatilities becomes sufficient to permit separation of the components.

By "conventional extractive distillation", it is meant that the components which have the higher and lower volatilities in the absence of the extractant retain their relative volatilities respectively when in the presence of the extractant; but the difference in volatilities between the components has increased. In a "conventional extractive distillation", HFC-143a, which has the higher volatility versus CFC-115 in the absence of an extractive agent, would still have the higher volatility in the presence of CFC-115 and the extractive agent. In such a "conventional extractive distillation", CFC-115 can be removed along with the extractive agent from the bottom of the distillation column, and HFC-143a can be removed in an overhead product stream.

There is a particular need for an extractive distillation procedure which will separate CFC-115, HFC-125 and CFC-12 from HFC-143a. We have found that these impurities can be efficiently separated from HFC-143a by using extractive distillation with an extractive agent comprising or consisting essentially of an alcohol such as at least one of methanol, butanol, ethanol, propanol, each of their corresponding isomers and cyclic compounds thereof, among others. While other compounds containing a hydroxyl (—OH) group can be used as an extractive agent, such compounds are less desirable than the aforementioned alcohols. Such alternate hydroxyl containing compounds would necessitate using relatively expensive apparatus and process conditions, e.g., thereby increasing energy costs.

We have found that HFC-125 is less volatile than HFC-143a in the presence of the alcohol extractive agent in spite of HFC-125 having a lower atmospheric pressure boiling point. Consequently, impurities such as HFC-125 can be removed from HFC-143a in the bottoms of an extractive distillation column along with the extractant. CFC-12 may also be removed in the bottoms of the extractive distillation column, separately or together with HFC-125.

We have also found that other fluorocarbon impurities such as HFC-32, HCFC-1113, HFC-143, HCFC-133a, HFC-134a, HCFC-142b, HFC-152a, HCFC-22, among others, can be removed from the HFC-143a concomitantly with lo the HFC-125 and/or CFC-12 by using the inventive process. This may be done in a single extractive distillation step since all these impurities have relative volatilities below that of the HFC-143a when in the presence of the alcohol extractant agents.

We have surprisingly found that CFC-115 is more volatile than the HFC-143a in the presence of these alcohol extractive agents in spite of CFC-115 having a higher atmospheric boiling point. CFC-115 can, therefore, be separated from HFC-143a by being removed as an overhead stream from the extractive distillation column while HFC-143a can be removed from the column bottoms along with the extractant.

We have found that ethane can be separated from HFC-143 a by being removed as a overhead stream from the extractive distillation column while HFC-143a can be removed from the column bottoms along with the extractant.

Consequently, separating several impurities which are more and less volatile than HFC-143a when in the presence of the extractant may require at least two extractive distillation steps. The various impurity combinations which may be removed in a single extractive distillation step and the necessary operating conditions are readily determined by those skilled in the art, using the information disclosed herein.

It was a surprising and an unexpected result that the alcohol containing extractive agent can permit the efficient removal of CFC-115, HFC-125 and/or CFC-12 from HFC-143a by extractive distillation. It was also surprising and unexpected that this agent can permit the concomitant removal of other fluorocarbon impurities selected from the group including HCFC-1113, HFC-32, HFC-143, HCFC-133a, HFC-134a, HCFC-142b, HFC-152a, HCFC-22, and ethane from the HFC-143 a, thereby eliminating the need for separate distillation steps.

In one aspect of the invention, a first mixture comprising HFC-143a and HFC-32 may be introduced to a distillation column which is operated under conditions that cause formation of an azeotropic or azeotrope-like composition between HFC-143a and HFC-32. Such compositions can be removed from the distillation column thereby purifying the remaining HFC-143a. Depending upon the quantity of HFC-32 relative to the quantity of HFC-143a in the first mixture, the azeotrope distillation can also be performed instead of, before and/or after the inventive extractive distillation method.

In another aspect of the invention, a first mixture comprising HFC-143 a and CFC-115 may be introduced to a distillation column which is operated under conditions that cause formation of an azeotropic or azeotrope-like composition between HFC-143a and CFC-115. Such compositions can be removed from the distillation column thereby purifying the remaining HFC-143a. Depending upon the quantity of CFC-115 relative to the quantity of HFC-143a in the first mixture, the azeotrope distillation can also be performed instead of, before and/or after the inventive extractive distillation method.

DETAILED DESCRIPTION

Figure 1:
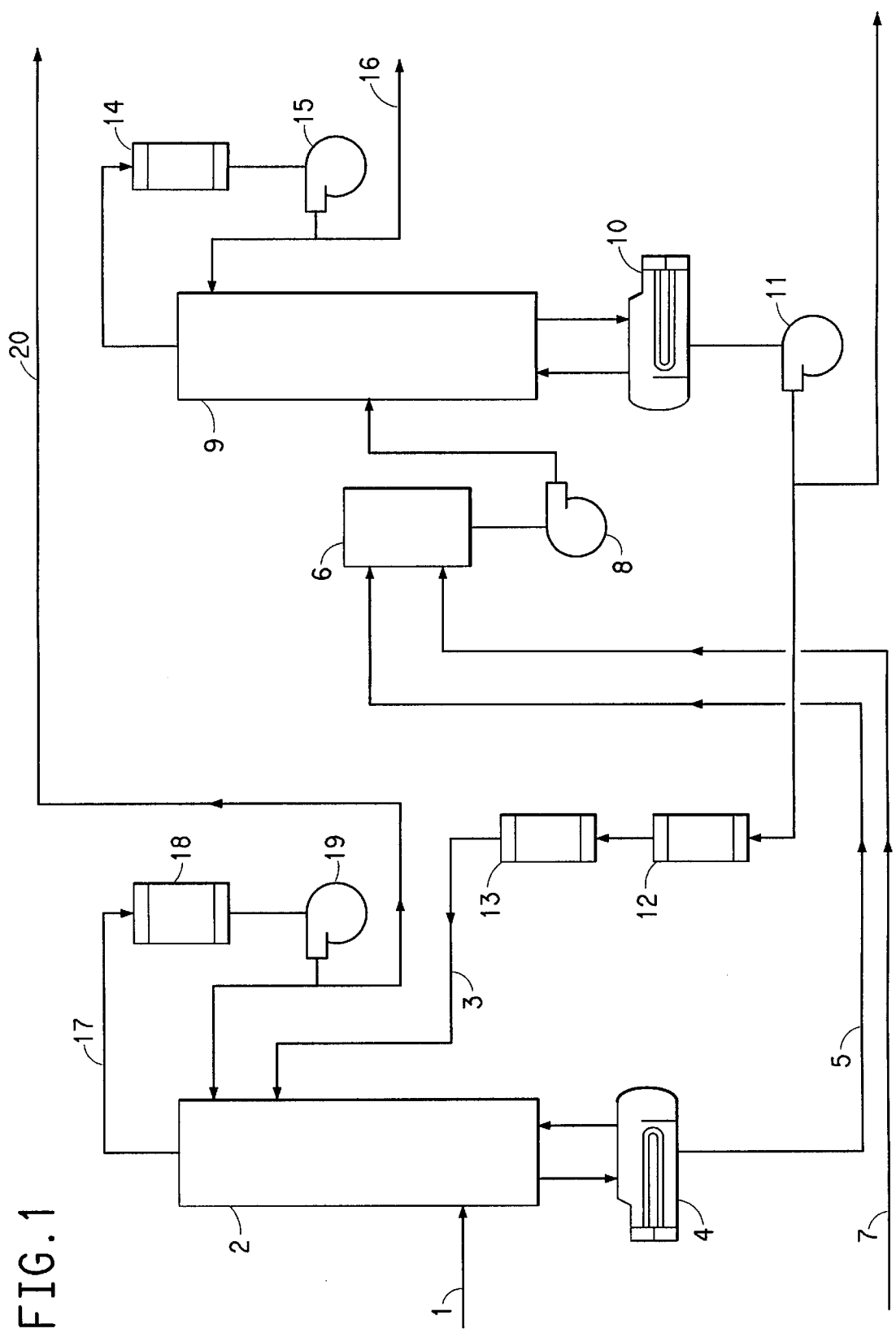
FIG. 1—FIG. 1 is a schematic diagram of an extractive distillation system that can be used for practicing the inventive process.

While the forthcoming disclosure places particular emphasis upon separating HFC-143a and CFC-115, the inventive process is also applicable to separating 143a and the other impurities disclosed herein.

By way of example, HFC-143a and CFC-115, which are the primary constituents of a first mixture, in their separated and pure states have normal boiling points of about −47.3 degrees C. and −39.1 degrees C., respectively. When combined, their relative volatility at around 0 degrees C. was found to be about 1.0 at a mole fraction of about 0.75 HFC-143a as shown below in Table 1, thereby indicating the formation of an azeotropic or azeotrope-like composition. These data indicate that it would be difficult or impossible to use conventional distillation procedures for separating both the HFC-143a and CFC-115 substantially free of the other. By "substantially free", it is meant that the desired HFC-143a product contains less than about 1.0 wt. % of the CFC-115 or other impurity, normally less than about 0.05 wt. %, and in some cases less than about 10 PPM by weight.

To determine the relative volatility of HFC-143a and CFC-115, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126; the entire disclosure of which is hereby incorporated by reference.

These measurements can be converted into equilibrium vapor and liquid compositions in the PTx cell by using an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids, 4th edition, publisher McGraw Hill, written by Reid, Prausnitz and Poling, on pages 241 to 387; and in "Phase Equilibria in Chemical Engineering, published by Butterworth Publishers, 1985, written by Stanley M. Walas, pages 165 to 244; the entire disclosure of each of the previously identified references hereby incorporated by reference.

Without wishing to be bound by any theory or explanation, it is believed that the NRTL equation can sufficiently predict whether or not HFC-143a and CFC-115 containing mixtures and/or the following other mixtures behave in an ideal manner, and can sufficiently predict the relative volatilities of the components in such mixtures.

The results of PTx measurements and the above series of calculations are summarized below in Tables 1 through 3, giving relative volatility for the HFC-143a/CFC-115 system, the methanol/HFC-143a system and the methanol/CFC-115 system, respectively. In Tables 1, 2 and 3 below, the "Relative Volatility" is that calculated by using the PTx cell pressure which was measured at the temperature indicated.

TABLE 1

Vapor-Liquid Measurements on the HFC-143a/CFC-115 System at 0 degrees C.

| Mole Fraction, HFC-143a | | Pressure | Relative Volatility |
|---|---|---|---|
| in Liquid | in Vapor | (psia) | HFC-143a/CFC-115 |
| 0.000 | 0.000 | 63.85 | 2.409 |
| 0.122 | 0.221 | 74.45 | 2.036 |
| 0.278 | 0.391 | 82.95 | 1.669 |
| 0.376 | 0.472 | 86.55 | 1.486 |
| 0.453 | 0.529 | 88.85 | 1.361 |
| 0.569 | 0.613 | 91.05 | 1.200 |
| 0.665 | 0.683 | 92.15 | 1.087 |
| 0.748 | 0.748 | 92.65 | 1.001 |
| 0.847 | 0.834 | 92.05 | 0.911 |

TABLE 1-continued

Vapor-Liquid Measurements on the HFC-143a/CFC-115 System at 0 degrees C.

| Mole Fraction, HFC-143a | | Pressure | Relative Volatility |
|---|---|---|---|
| in Liquid | in Vapor | (psia) | HFC-143a/CFC-115 |
| 0.914 | 0.901 | 91.45 | 0.856 |
| 0.979 | 0.974 | 89.80 | 0.808 |
| 1.000 | 1.000 | 89.45 | 0.794 |

The "Mole Fraction" column refers to the quantity of HFC-143a that is in the liquid and vapor portions of the HFC-143a/CFC-115 mixture within the PTx Cell. By virtue of a pressure maxima, and of a point wherein the relative volatility equals 1, the data show the existence of an azeotropic or azeotrope-like mixture at this temperature and a composition of about 0.75 mole fraction of HFC-143a.

At relatively low concentrations of HFC-143a, the relative volatility of HFC-143a to CFC-115 is sufficient to permit enriching the overhead concentration of HFC-143a by using conventional distillation methods. However, at compositions approaching 75 mole % HFC-143a, the relative volatility approaches 1.0, indicating that separating HFC-143a from HFC-125 by conventional distillation becomes increasing difficult, e.g., conventional distillation would require using large and expensive distillation columns. At the azeotrope point of 75 mole % 143a, the relative volatility is 1.0, indicating that separation by conventional distillation is essentially impossible.

The results of PTx measurements and the above series of calculations are summarized below in Tables 2 through 3, giving relative volatilities for the HFC-143a/methanol and the CFC-115/methanol systems. In Tables 2 and 3 below, the "Relative Volatility" is that calculated by using the PTx cell pressure which is measured at the temperature indicated.

TABLE 2

Vapor-Liquid Measurements on the HFC-143a/Methanol System at 11.2 degrees C.

| Mole Fraction, Methanol | | Pressure | Relative Volatility |
|---|---|---|---|
| in Liquid | in Vapor | (psia) | HFC-143a/Methanol |
| 0.000 | 0.0000 | 125.88 | 3.35 |
| 0.070 | 0.0086 | 123.43 | 8.77 |
| 0.162 | 0.0095 | 121.75 | 20.20 |
| 0.271 | 0.0093 | 120.35 | 39.52 |
| 0.393 | 0.0094 | 118.46 | 68.49 |
| 0.582 | 0.0103 | 112.36 | 135.13 |
| 0.747 | 0.0124 | 96.44 | 238.09 |
| 0.849 | 0.0165 | 74.10 | 344.82 |
| 0.947 | 0.0337 | 34.56 | 526.31 |
| 1.000 | 1.000 | 1.14 | 666.66 |

The "Mole Fraction" column refers to the quantity of methanol that is in the liquid and vapor portions of the HFC-143a/Methanol mixture within the PTx Cell.

TABLE 3

Vapor-Liquid Measurements on the CFC-115/Methanol System at 20 degrees C.

| Mole Fraction, Methanol | | Pressure | Relative Volatility |
|---|---|---|---|
| in Liquid | in Vapor | (psia) | CFC-115/Methanol |
| 0.000 | 0.000 | 114.90 | 0.69 |
| 0.099 | 0.024 | 115.10 | 4.50 |
| 0.896 | 0.020 | 115.10 | 421.94 |

TABLE 3-continued

Vapor-Liquid Measurements on the CFC-115/Methanol System at 20 degrees C.

| Mole Fraction, Methanol | | Pressure | Relative Volatility |
|---|---|---|---|
| in Liquid | in Vapor | (psia) | CFC-115/Methanol |
| 0.913 | 0.021 | 110.90 | 499.1 |
| 0.936 | 0.023 | 100.20 | 643.2 |
| 0.958 | 0.027 | 82.80 | 833.33 |
| 0.980 | 0.041 | 51.40 | 1129. |
| 1.000 | 1.000 | 1.89 | 1559. |

The "Mole Fraction" column refers to the quantity of methanol that is in the liquid and vapor portions of the CFC-115/Methanol mixture within the PTx Cell.

A comparison of Tables 2 and 3 shows that as the amount of methanol in the fluorocarbon increases, the relative volatility of HFC-143 a versus methanol and the relative volatility of CFC-115 versus methanol are affected differently. As the mole fraction of methanol in both binary mixtures is increased, the calculated relative volatility of CFC-115 to methanol becomes much greater than that of HFC-143a to methanol, thereby indicating that adding an extractive agent such as methanol to a mixture comprising HFC-143a and CFC-115 will greatly affect the relative volatility of these two compounds to each other. These PTx measurements were employed to develop the extractive distillation examples which are described below in greater detail.

It was a surprising and an unexpected result that the instant invention can successfully employ simple alcohols such as methanol and ethanol as extractive distillation agent for separating HFC-143a from CFC-115. Even more surprising was the manner in which the inventive extractive agent(s) functions, because HFC-143a, which in the absence of the extractive agent(s) has a higher volatility than CFC-115, has a lower volatility versus CFC-115 when in the presence of the extractive agent(s) of the invention. Specifically, the extractive agent of the invention surprisingly causes the expected or predicted relative volatilities of HFC-143a and CFC-115 to be reversed, wherein HFC-143a can be removed along with the extractive agent from the bottom of an extractive distillation column, and CFC-115 can be removed in an overhead product stream.

The instant invention solves the problems associated with conventional distillation methods by employing an extractive distillation process for separating HFC-143a from a first mixture containing HFC-143a and at least one fluorocarbon impurity selected from CFC-115, HFC-125, and CFC-12 wherein the process comprises:

(i) adding an extractive distillation agent comprising an alcohol having an atmospheric boiling point greater than about 64 degrees C. and less than about 100 degrees C., to the first mixture in order to form a second mixture;

(ii) separating the HFC-143a from the second mixture by extractively distilling the second mixture in an extractive distillation zone thereby recovering a HFC-143a containing stream that is substantially free of at least one of the fluorocarbon impurities.

(iii) separating the HFC-143a from the extractive agent to yield a HFC-143a product.

By "substantially free" it is meant that the HFC-143a contains less than about 1.0 wt %, normally less than 0.5 wt %, and in some cases less than 10 PPM of one of the fluorocarbon impurities.

The first mixture can be obtained from any suitable manufacturing process or source. The extractive agents used in the present invention are commercially available. If desired, the alcohol extractive agents of the invention can be removed from the HFC-143a by using conventional distillation methods. For example, an ethanol or a methanol extractive agent can be removed from HFC-143a and recycled to the distillation column for separating additional quantities of HFC-143a. Further, these alcohols are soluble in water so that even traces of the extractive agent can be readily removed from the HFC-143a by extracting or scrubbing with water.

Representative alcohols which are suitable for use as an extractive agent comprise or consist essentially of those containing 1 to 4 carbon atoms and having an atmospheric boiling point between about 64 and about 100 degrees C., e.g., aliphatic alcohols. Specific examples of such alcohols comprise or consist essentially of at least one member selected from the group of methanol, ethanol, n-propanol, isopropanol, sec-butanol, tert-butanol, among others.

By employing the inventive alcohol containing extractive agent, the problems associated with conventional distillation methods can be solved. "conventional distillation" is intended to refer to a process wherein the relative volatility only of the components in the mixture to be separated is being used for separation, whereas "extractive distillation" depends upon the ability of certain extractive agents to amplify or increase the relative volatility of the compounds to be separated, either in the same direction as the original compounds or, in some cases, in the opposite direction. Extractive distillation is typically performed by operating a continuous distillation column, which comprises a multi-stage distillation column, with a minimum of two feed points, e.g. introducing the extractive agent at a first feed point which is located above the second feed point that is used for introducing the mixture to be separated, a reboiler, an overhead condenser for returning reflux to the column, among other commercially available apparatus.

In one aspect of the invention, an extractive agent, e.g. methanol, is introduced at an upper feed point of an extractive distillation column, whereas the first mixture requiring separation, e.g., comprising HFC-143a and CFC-115, is introduced at a relatively lower point in the column. The liquid extractive agent passes downwardly through trays, which are located in the center of the column, in order to contact the first mixture thereby forming a second mixture. While in the presence of the extractive agent, CFC-115 is relatively more volatile than HFC-143a, thereby allowing CFC-115 substantially free of HFC-143a to exit the top of the column. The CFC-115, which is exiting the top of the column, can be condensed by using conventional reflux condensers. At least a portion of this condensed stream can be returned to the top of the column as reflux, and the remainder recovered as a useful product, e.g., substantially pure CFC-115. If desired, the CFC-115 can be transported to a second extractive distillation column and/or a second conventional distillation column for further purification. For example, the recovered CFC-115 can be transported to a second extractive distillation column for removing fluorocarbon impurities.

HFC-143a, extractive agent and optionally other fluorocarbon impurities comprise a third mixture that exits from the bottom of the extractive instillation column which can in turn then be passed to a stripper or conventional distillation column for further separation by using conventional distillation or other known methods. If desired, the extractive agent may then be recycled to the extractive distillation column. In some cases, after removing the extractive agent by conventional distillation HFC-143a is recovered as a useful product. The recovered HFC-143a can also be transported to a second or third conventional and/or extractive distillation column for removing additional fluorocarbon impurities, e.g., obtaining substantially pure HFC-143a.

If desired, the extractive agent can be removed by any expedient method such as water extraction. For example, a mixture of HFC-143a and alcohol is passed through water whereby the alcohol is preferentially withdrawn from the mixture.

Depending upon the relative quantity of HFC-143a and CFC-115 in the first mixture, HFC-143a can be removed from a mixture containing relatively large quantities of CFC-115, or vice versa, thereby producing the desired product substantially free of impurities.

The ratio of the material exiting the top of the extractive distillation column, which is then condensed and in turn returned to the column, to the amount of material that is removed as product is commonly referred to known as the reflux ratio. The reflux ratio will define the physical characteristics of the extractive distillation column. In general, an increase in the reflux ratio will in turn cause an increase in the purity of the recovered CFC-115, e.g., the quantity of extractant in the recovered CFC-115 can be reduced if not eliminated.

The specific conditions that can be used for practicing the invention depend upon a number of interrelated design parameters such as the diameter of the column, selected feed points, the number of separation stages in the column, among other parameters. The operating pressure of the distillation system may range from about 15 to 350 psia, normally about 50 to 300 psia. Typically, an increase in the extractant feed rate relative to the mixture to be separated, or an increase in the reflux ratio will result in an increase in the purity of the overhead product produced, e.g., an increase in the extractant feed rate relative to the mixture to be separate will increase the removal efficiency of HFC-143a from the CFC-115 exiting the top of the column, while increasing the reflux ratio will increase the removal efficiency of the extractant from the CFC-115 exiting the top of the column. The temperature and heat transfer area of the overhead condenser is normally sufficient to substantially fully condense the overhead product, or is optionally sufficient to achieve the desired reflux ratio by partial condensation.

The temperature that is employed at a given step in the inventive process is a function of the pressure and the design characteristics of the distillation column, e.g., the ratio of extractive agent to the first mixture. Typically, the temperature will range from about −25° to about 200° C. based upon an operating pressure of about 200 psia.

The quantity of fluorocarbon impurities in the first mixture, i.e., a mixture comprising HFC-143a and CFC-115, can be reduced by using conventional distillation if the composition differs from that of an HFC-143a/CFC-115 azeotrope. However, conventional distillation processes are incapable of completely separating HFC-143a and CFC-115 because of the barrier imposed by the azeotrope. Conventional distillation can also be used for reducing the initial quantity of other such fluorocarbon impurities. That is, conventional distillation can be used for removing relatively large or bulk quantities of fluorocarbon impurities from the first mixture which in turn is processed in accordance with the inventive process for separating HFC-143a and CFC-115.

Similar difficulties to those encountered in the separation of HFC-143a and CFC-115 exist in the separation of HFC-125 and HFC-143a, and in the separation of HFC-143a and CFC-12.

By applying the inventive process to the separation of HFC-125 from HFC-143a, it is found that the extractive agent again reverses the inherent relative volatility of the pair. The HFC-143a, with a slightly higher normal boiling point, becomes more volatile than the HFC-125. The purified HFC-143a can exit the extractive distillation column in an overhead stream, while the HFC-125 can exit in the column bottoms along with the extractive agent. The removal of HFC-125 from HFC-143a is nearly impossible by conventional distillation.

By applying the inventive process to the separation of CFC-12 and HFC-143a, the extractive agent acts to reinforce and amplify the inherent relative volatilities of the pair. The HFC-143a, inherently more volatile than the CFC-12, can exit the extractive distillation column in an overhead stream, while the CFC-12 can exit in the column bottoms along with the extractive agent. The removal of CFC-12 from HFC-143a by conventional distillation is typically impractical because of required high reflux ratios and refining losses.

The inventive process may also be employed to simultaneously or sequentially remove a number of impurities from HFC-143a.

By applying the inventive process to the separation of HCFC-1113 and HFC-143a, the extractive agent again acts to reinforce and amplify the inherent relative volatilities of the pair. The HFC-143a, inherently more volatile than the HCFC-1113, can exit the extractive distillation column in an overhead stream, while the HCFC-1113 can exit in the column bottoms with the extractive agent. The removal of HCFC-1113 from HFC-143a by conventional distillation is feasible; but undesirable since losses of HFC-143a are large with low reflux ratios.

By applying the inventive process to the separation of HCFC-22 and HFC-143a, and to the separation of ethane and HFC-143a, the extractive agent again acts to reinforce and amplify the inherent relative volatilities of each of the components in the respective pairs.

Similarly, this inventive process may be used for separating HFC-32, HFC-143, HCFC-133a, HFC-134a, HCFC-142b, and/or HFC-152a from the HFC-143a. While these impurities can also be removed from HFC-143a by conventional distillation, they are more conveniently removed during the extractive distillation for removal of HFC-125, CFC-12, HCFC-1113, and/or HCFC-22 since any or all of these impurities can be removed simultaneously, thus avoiding unnecessary process steps. Their relative volatilities act in the same direction relative to the HFC-143a. That is, these impurities are less volatile than the HFC-143a in the presence of the extractive agent and, therefore, can be removed in the bottoms stream together with the extractant while a purified HFC-143a can be removed in an overhead stream.

If the stream of HFC-143a to be purified includes one or more compounds that are less volatile than HFC-143a, e.g. HFC-125, and some compounds that are more volatile than HFC-143a in the presence of the extractive agent, e.g. CFC-115, these impurities can be removed in a two separate applications of the inventive process. For example, the CFC-115 can be separated from the HFC-143a and HFC-125 when operating an extractive distillation under conditions wherein the HFC-143a and HFC-125 exit in the bottoms of a column with the alcohol extraction, while the CFC-115 exits the top. The HFC-143a and HFC-125 can be separated from the alcohol extractant by any convenient means, e.g., by scrubbing the HFC-143a/HFC-125 mix with water to remove the alcohol, then drying the HFC-143a/BFC-125 mixture. The HFC-143a/HFC-125 mixture can then be fed to an extractive distillation column, which uses alcohols as an extractant that is operated under conditions wherein HFC-143a would exit the top and HFC-125 would exit the bottoms along with the alcohol extractant. Consequently, the instant invention can employ one or more of extractive distillation, convention distillation, and azeotropic distillation to tailor a process wherein a virtually unlimited array of impurities can be separated from each other and HFC-143a.

Certain aspects of the invention can be better understood by reference to the Figures. Referring now to the Figures, FIG. 1 schematically illustrates a system which can be used for performing one aspect of the inventive distillation process. A first mixture comprising HFC-143a and CFC-115 is supplied via conduit 1 to extraction column 2. At least one liquid extractive agent is supplied via conduit 3 to the extraction column 2, and introduced into column 3 at a location above the mixture 1. A second mixture comprising the extractive agent(s) and HFC-143a is removed from the bottom of column 2 and transported to steam-heated reboiler 4. In some cases, the reboiler 4 is attached to the extractive column 2. The second mixture is supplied via conduit 5 to a feed tank 6. Supplemental liquid extractive agent can also supply to feed tank 6 via conduit 7 thereby forming a third mixture or extractive agent recycle. A pump 8 transports the third mixture to a stripping mixture column 9. Stripping column 9 separates the extractive agents from non-extractive agents. Extractive agent is removed from column 9 and supplied to a second steam heated reboiler 10. In some cases, the reboiler 10 is attached to column 9. Pump 11 transports the extractive agent from the reboiler 10 through a cold water chiller 12, and then to chiller 13. If necessary, excess quantities of extractive agent can be purged prior to reaching chiller 12. Typically, chiller 13 is operated at a temperature of about −25° C. After exiting chiller 13, the extraction agent is supplied via conduit 3 into extraction column 2.

HFC-143a exits from the top of stripping column 9 as an off gas, and is introduced into condenser 14, which is typically operated at a temperature of about −25° C. While under reflux conditions, pump 15 returns a portion of the HFC-143a to the stripping column 9. The remaining portion of the HFC-143a can be removed from the system via conduit 16.

An off gas is also removed from extraction column 2. The off gas can be, for example, CFC-115 that is substantially free of HFC-143a and other fluorocarbons. The CFC-115 is transported via conduit 17 to condenser 18. Condenser 18 is typically operated at a temperature of about −25° C. While under reflux conditions, pump 19 returns a portion of the CFC-115 to extraction column 2. The CFC-115 can be removed from the system via conduit 20.

In a second aspect of the invention, a system is operated in substantially the same manner as the system in FIG. 1 with the exception that the first mixture in conduit 1 comprises HFC-143a and one or more impurities selected from HFC-125, CFC-12, HCFC-22, HCFC-1113, HFC-32, HFC-143, HCFC-133a, HFC-134a, HCFC-142b and HFC-152a. In this system, the impurities exit the bottom of extractive distillation column 2 as a mixture with the extractive agent, e.g., methanol. The mixture with methanol is transported via conduit 5 to distillation column 9 for separating the impurities and methanol. The HFC-143a product leaves the top of the extractive distillation column 2. In some cases, the HFC-143a stream in conduit 16 and/or 20 is transported to a third conventional or extractive distillation column for removal of either additional or remaining halocarbon impurities.

While the best results are normally obtained by operating the inventive process at process conditions that minimize formation of azeotropic or azeotrope-like compositions, such compositions may be used to purify HCFC-143a, HFC-125, CFC-115 and/or HFC-32. The azeotropic or azeotrope-like compositions that can be formed include one or more of the following mixtures: HFC-143a/CFC-115, HFC-143a/HFC-125, HFC-143a/HFC-32; among others.

Whenever used in the specification and appended claims the terms below are intended to have the following definitions.

By "azeotrope" or "azeotropic" composition is meant a constant boiling liquid admixture of two or more substances that behaves as a single substance. One way to characterize an azeotropic composition or mixture is that the vapor produced by partial evaporation or distillation of the liquid has the same composition as the liquid from which it was evaporated or distilled, e.g., the admixture distills/refluxes without compositional change. Constant boiling compositions are characterized as azeotropic because they exhibit either a maximum or minimum boiling point, as compared with that of the non-azeotropic mixtures of the same components. An azeotropic composition can also be characterized as the maximum or minimum vapor pressure for a mixture at a given temperature when plotted as a function of mole fraction.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, e.g., the admixture distills/refluxes without substantial compositional change. An azeotrope-like composition can also be characterized by the area, which is shown by plotting vapor pressure at given temperature as a function of mole fraction, that is adjacent to the maximum or minimum vapor pressure.

Typically, a composition is azeotrope-like, if, after about 50 weight percent of the composition is removed such as by evaporation or boiling off, the change between the original composition and the composition remaining is less than about 6% and normally less than about 3% relative to the original composition.

By "effective amount" is intended to refer to the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points. Effective amount also includes the amounts, such as may be expressed in weight percentages, of each component of the compositions of the instant invention which form azeotropic or azeotrope-like compositions at temperatures or pressures other than as described herein. Therefore, included in this invention are azeotropic or azeotrope-like compositions consisting essentially of effective amounts of HFC-143a and at least one fluorinated molecule such that after about 50 weight percent of an original composition is evaporated or boiled off to produce a remaining composition, the change between the original composition and the remaining composition is typically no more than about 6% and normally no more than about 3% or less relative to the original composition.

It is possible to characterize, in effect, a constant boiling admixture which may appear under many guises, depending upon the conditions chosen, by any of several criteria:

The composition can be defined as an azeotrope of HFC-143a ("A") and a fluorinated halocarbon ("B"), among others, because the term "azeotrope" is at once both definitive and limitative, and requires effective amounts of A,B for this unique composition of matter which can be a constant boiling composition.

It is well known by those skilled in the art, that, at different pressures, the composition of a given azeotrope will vary at least to some degree, and changes in pressure will also change, at least to some degree, the boiling point temperature. Thus, an azeotrope of HFC-143a ("A") and a fluorinated halocarbon ("B"), among others, represents a unique type of relationship but with a variable composition which depends on temperature and/or pressure. Therefore, compositional ranges, rather than fixed compositions, are often used to define azeotropes.

The composition can be defined as a particular weight percent relationship or mole percent relationship of HFC-143a ("A") and a fluorinated halocarbon ("B"), among others, while recognizing that such specific values point out only one particular relationship and that in actuality, a series of such relationships, represented by A,B actually exist for a given azeotrope, varied by the influence of pressure.

An azeotrope of HFC-143a ("A") and a fluorinated halocarbon ("B"), among others, can be characterized by defining the compositions as an azeotrope characterized by a boiling point at a given pressure, thus giving identifying characteristics without unduly limiting the scope of the invention by a specific numerical composition, which is limited by and is only as accurate as the analytical equipment available.

The azeotrope or azeotrope-like compositions of the present invention may be formed by operating a conventional distillation apparatus, when practicing the inventive extractive distillation method, and by combining effective amounts of the components by any convenient method including mixing, combining, among others. For best results, a preferred method is to weigh the desired component amounts, and thereafter combine them in an appropriate container.

We have found that azeotropic or azeotrope-like compositions or mixtures can form between HFC-143a and CFC-115 at a variety of temperatures and pressures. For example, an azeotropic or azeotrope-like composition may be formed between a mixture consisting essentially of about 73.3 to about 90.8 mole % HFC-143a and about 26.7 to about 9.2 mole % CFC-115 when at a temperature of about −65 to about 70 degrees C. and a vapor pressure of about 6.1 to about 515 psia.

Conventional distillation methods may be capable of separating an HFC-143a and CFC-115 containing mixture that includes more than the azeotropic or azeotrope-like concentration of HFC-143a, when such methods are performed at a specific temperature and pressure. For example, substantially pure HPC-143a can be produced by distilling a mixture having more than about 75 mole % HFC-143a at a temperature of 0 degrees C., thereby forming an azeotropic or azeotrope-like composition which can be removed from the top of the distillation column. Substantially pure HFC-143a can be recovered from the distillation column as a bottoms product. In other words, forming the HFC-143a/CFC-115 azeotropic or azeotrope-like composition may permit distilling a mixture comprising HFC-143a and CFC-115 and removing the CFC-115 as an HFC-143a/CFC-115 azeotrope. By removing CFC-115 as a component of an azeotropic or azeotrope-like composition, substantially pure HFC-143a may be obtained, e.g. at least about 99.99% by weight HFC-143a.

HFC-143a and CFC-115 can each be purified by employing the above-identified azeotropic or azeotrope-like compositions in an conventional distillation column. For example, a conventional distillation column can be operated at a temperature and pressure which causes these azeotropes to form. The azeotropic or azeotrope-like composition has a minimum boiling point, and the composition can be collected from the column as an overhead product. For example, when HFC-143a is present in excess of its azeotropic or azeotrope-like compositions with CFC-115, an azeotropic or azeotrope-like composition consisting essentially of HFC-143a and CFC-115 is collected as an overhead product, thereby leaving substantially pure HFC-143a in the column bottoms. Conversely, when CFC-115 is present in excess of its azeotrope compositions with HFC-143a, an azeotropic or azeotrope-like composition consisting essentially of HFC-143 a and CFC-115 is collected as an overhead product, thereby leaving substantially pure CFC-115 as a bottoms product.

The recovered composition, if desired, can be used as the first mixture or feed stream that is processed in accordance with the inventive process described above, e.g., the azeotropic distillation can be used for removing bulk quantities of a fluorocarbon impurity wherein the azeotrope is in turn separated by using extractive distillation.

When performing the previously described azeotropic distillation methods, a significant amount of the HFC-143a can remain within the azeotropic or azeotrope-like composition. The specific amount depends upon the amount of CFC-115 in the first or starting mixture. The quantity of HFC-143a remaining in the azeotropic or azeotrope-like composition is a function of the amount of HFC-143a relative to the CFC-115 in the first mixture, e.g., the quantity of HFC-143a remaining in the azeotrope increases with increased amount of CFC-115 in the first mixture. The azeotropic or azeotrope-like composition, if desired, can be recovered as a useful product, e.g., for use as a refrigerant, blowing agent, or other uses. The recovered composition, if desired, can be used as the first mixture or feed stream that is processed in accordance with the inventive process described above, e.g., the azeotropic distillation can be used for removing bulk quantities of a fluorocarbon impurity wherein the azeotrope is in turn separated by using extractive distillation. In the event that it is preferable to obtain either substantially pure HFC-143a or CFC-115, then the extractive distillation method of this invention should be practiced, i.e., the relative volatility for such compositions is sufficiently close to 1.0 that an impractically large distillation column would otherwise be required for separation using conventional distillation.

The following Examples are provided to illustrate certain aspects of the present invention; but not limit the scope of the appended claims. Parts per million (PPM) concentrations are by weight of fluorocarbons, i.e. are given on an extractant-free basis, unless specified otherwise. The recovery % is the % of fresh feed, unless specified otherwise. The following Examples employ the NRTL interaction parameters identified above. In the following Examples, each stage is based upon a 100% operational or performance efficiency. Differing column designs and operating conditions are employed in the extractive distillation than in the Comparative Example in order to maximize the performance of each distillation method. Each Comparative Example shows a conventional distillation and is followed immediately by an Example which shows using the extractive distillation of the invention being applied to the same starting composition. In all examples, the column condenser is counted as stage no. 1.

COMPARATIVE EXAMPLE 1

In this comparative example, conventional distillation within a column with 62 stages is used for purifying a feed stream containing 1000 Lb./hr of HFC-143a with 111 Lb./hr of CFC-115 (10 wt. %). The feed is introduced on stage 25 at a temperature of −20 degrees C., with the column condenser pressure at 34.7 psia and the column base pressure 3 psi higher. The distillate temperature varies from −28.9 to −28.3 degrees C., depending on the reflux flow, and the bottom column temperature is −25.3 degrees C.. Under these operating conditions, the HFC-143a/CFC-115 azeotrope or a mixture thereof with HFC-143a leaves in the overhead (distillate) stream from the column. The remaining HFC-143a product exits in the bottoms tails stream. Conditions are set so as to meet a composition of 100 parts per million (PPM) of CFC-115 in the HFC-143a bottoms product, and the reflux flow is varied to show the effect on HFC-143a product recovery.

The results of using this conventional distillation method are shown below in Table 4.

EXAMPLE 1

In this Example of the invention, an extractive distillation column with 57 stages is used for purifying a feed stream with the same composition as in Comparative Example 1. The feed is introduced on stage 40 and the methanol extractant on stage 20, both at a temperature of −20 degrees C., with the column condenser pressure at 34.7 psia and the column base pressure 3 psi higher. The distillate temperature is about −18.1 degrees C., and the bottom column temperature varies from 67.2 to 44.2 degrees C. depending of the extractant flow. Under these operating conditions, the HFC-143a product will leave in the bottoms (tails) stream from the column with methanol. The CFC-115 exits in the distillate (overhead) stream. Conditions are set so as to meet a composition of 1 part per million (PPM) of CFC-115 in the HFC-143a bottoms product, and the extractant feed rate is varied to show the effect on distillate product purity.

The results of using this inventive extractive distillation process are shown below in Table 5.

TABLE 4

REMOVAL OF CFC-115 FROM HFC-143a

| Reflux | Distillate | | | Tails or Bottoms | | | Dist. | % of 143a |
|---|---|---|---|---|---|---|---|---|
| Flow (pph) | 143a (pph) | 115 (pph) | Temp (C.) | 143a (pph) | 115 (PPM) | Temp (C.) | 143a (WT.) | in Feed Recovered as Bottoms Product |
| 20000 | 155 | 111 | −28.9 | 845 | 100 | −25.3 | 58.2 | 84.5 |
| 10000 | 155 | 111 | −28.9 | 845 | 100 | −25.3 | 58.4 | 84.5 |
| 5000 | 159 | 111 | −28.3 | 841 | 100 | −25.3 | 58.9 | 84.1 |

While the HFC-143a product specification is met in the tails product, the HFC-143a/CFC-115 azeotrope is taken overhead as the distillate, thereby reducing HFC-143a recovery. The recovery efficiency of the HFC-143a is

TABLE 5

REMOVAL OF CFC-115 FROM HFC-143a

| Extr. | Reflux | Distillate | | | | Tails or Bottoms | | | % of 143a |
|---|---|---|---|---|---|---|---|---|---|
| Flow (pph) | Flow (pph) | 115 (pph) | 143a (PPM) | Extr (PPM) | Temp (C.) | 115 (PPM) | 143a (pph) | Temp (C.) | in Feed Recovered as Bottoms Product |
| 30000 | 2500 | 111 | 0.2 | 0.30 | −18.1 | 1.0 | 1000 | 67.2 | 100 |
| 25000 | " | 111 | 0.3 | 0.30 | −18.1 | 1.0 | 1000 | 62.1 | 100 |
| 20000 | " | 111 | 1.0 | 0.29 | −18.1 | 1.0 | 1000 | 54.9 | 100 |
| 15000 | " | 111 | 5.7 | 0.29 | −18.1 | 1.0 | 1000 | 44.2 | 100 | reduced because an azeotropic or azeotrope-like composition is formed between HFC-143a and CFC-115 that exits the column as the distillate in this Comparative Example. The distillate CFC-115 purity is therefore relatively low. However, this Comparative Example illustrates how these HFC-143a/CFC-115 azeotropic compositions can be used to remove CFC-115 from an HFC-143 a containing mixture, e.g., thereby producing substantially pure HFC-143a by reducing the concentration of CFC-115 in the first mixture.

When employing methanol in an extractive distillation, the methanol surprisingly reverses the normal relative volatilities of HFC-143a and CFC-115, so that CFC-115 is the overhead product in spite of its higher normal boiling point. Both the HFC-143a and the CFC-115 can be recovered as substantially pure products. This Example illustrates a 100 times improvement in the purity of HFC-143a, an improved recovery of HFC-143a, and a higher distillate purity versus Comparative Example 1.

COMPARATIVE EXAMPLE 2

In this Comparative Example, conventional distillation within a column with 62 stages is used for purifying a feed stream containing 1000 Lb./hr of HFC-143a with 5.025 Lb./hr of HFC-125 (5000 PPM by weight), i.e. removing trace quantities of HFC-125 from HFC-143a. The feed is introduced on stage 30 at a temperature of −20 degrees C., with the column condenser pressure at 34.7 psia n base pressure 3 psi higher. The distillate temperature is about −27.4 degrees C. and the bottom column temperature is −25.2 to −25.3 degrees C. depending on the distillate to feed ratio. Conditions are set so as to obtain a composition of 100 parts per million (PPM) of HFC-125 in the HFC-143a distillate product, and the distillate to feed ratio (based on HFC-143 a in the feed) is varied to show the effect on HFC-143a product recovery and purity.

The results of using this conventional distillation method are shown below in Table 6.

EXAMPLE 2

In this Example of the invention, an extractive distillation column with 57 stages is used for purifying a feed stream with the same composition as in Comparative Example 2. The feed is introduced on stage 40 and the methanol extractant on stage 20, both at a temperature of −20 degrees C., with the column condenser pressure at 34.7 psia and the column base pressure 3 psi higher. The distillate temperature is about −27.4 degrees C., and the bottom column temperature varies from 90.5 to 90.4 degrees C. depending of the extractant flow. Under these operating conditions, the HFC-143 a product will leave in the distillate (overhead) stream from the column. The HFC-125 exits in the bottoms (tails) stream with the extractant. Conditions are set so as to meet a composition of below 25 part per million (PPM) of HFC-125 in the HFC-143a distillate product, and the extractant feed rate is varied to show the effect on distillate product purity.

The results of using this inventive extractive distillation process are shown below in Table 7.

TABLE 6

REMOVAL OF HFC-125 FROM HFC-143a

| Reflux | Distillate | | | Tails or Bottoms | | | Dist. | % of 143a |
|---|---|---|---|---|---|---|---|---|
| Flow (pph) | 143a (pph) | 125 (PPM) | Temp (C.) | 143a (pph) | 125 (pph) | Temp (C.) | 143a (WT. %) | in Feed Recovered As Distillate Product |
| 100000 | 949 | 1566 | −27.4 | 51 | 3.5 | −25.2 | 93.5 | 95 |
| " | 899 | 924 | −27.4 | 101 | 4.2 | −25.2 | 96.0 | 90 |
| " | 800 | 522 | −27.4 | 200 | 4.6 | −25.3 | 97.8 | 80 |
| " | 500 | 249 | −27.4 | 500 | 4.9 | −25.3 | 99.0 | 50 |
| " | 200 | 174 | −27.4 | 800 | 5.0 | −25.3 | 99.4 | 20 |
| " | 100 | 159 | −27.4 | 900 | 5.0 | −25.3 | 99.4 | 10 |
| " | 50 | 153 | −27.4 | 950 | 5.0 | −25.3 | 99.5 | 5 |

Even when employing a very high reflux flow and allowing high HFC-143a losses in the tails, the HFC-143a product specification is not met at any condition. For all practical purposes, this separation appears to be impossible by conventional distillation because a high-boiling azeotropic or azeotrope-like composition is formed between HFC-125 and HFC-143a that exits the column as the bottoms (tails) in this Comparative Example. However, this Comparative Example illustrates how these azeotropic compositions can be used to remove HFC-125 from an HFC-143a containing mixture, e.g., thereby producing substantially pure HFC-143a in the distillate by reducing the concentration of HFC-125 in the first mixture.

TABLE 7

REMOVAL OF HFC-125 FROM HFC-143a

| Extr. | Reflux | Distillate | | | | Tails or Bottoms | | | % of 143a |
|---|---|---|---|---|---|---|---|---|---|
| Flow (pph) | Flow (pph) | 125 (PPM) | 143a (pph) | Extr (PPM) | Temp (C.) | 125 (pph) | 143a (PPM) | Temp (C.) | in Feed Recovered as Distillate Product |
| 80000 | 5000 | 9 | 1000 | 0.0 | −27.4 | 5.0 | 1204 | 90.5 | 100 |
| 60000 | " | 10 | 1000 | 0.0 | −27.4 | 5.0 | 1352 | 90.5 | 100 |
| 40000 | " | 11 | 1000 | 0.0 | −27.4 | 5.0 | 1560 | 90.5 | 100 |
| 30000 | " | 14 | 1000 | 0.0 | −27.4 | 5.0 | 1970 | 90.5 | 100 |
| 20000 | " | 21 | 1000 | 0.0 | −27.4 | 5.0 | 2930 | 90.4 | 100 |

The methanol reverses the relative volatility of these two compounds, and the higher boiling HFC-143a is distilled overhead. High-purity HFC-143a (distillate) is produced at all extractant flows, with an extremely high rate of recovery, even though this separation is virtually impossible by conventional distillation.

COMPARATIVE EXAMPLE 3

In this Comparative Example, conventional distillation within a column with 62 stages is used for purifying a feed stream containing 1000 Lb./hr of HFC-143a with 5.025 Lb./hr of CFC-12 (5000 PPM by weight). The feed is introduced on stage 30 at a temperature of −20 degrees C., with the column condenser pressure at 34.7 psia and the column base pressure 3 psi higher. The distillate temperature is about −27.4 degrees C., and the bottom column temperature varies from about −6.7 degrees C. to about −25.3 degrees C. depending on the reflux flow. Conditions are set so as to meet a composition of 100 parts per million (PPM) of CFC-12 in the HFC-143 a distillate product.

The results of using this conventional distillation method are shown below in Table 8.

TABLE 8

REMOVAL OF CFC-12 FROM HFC-143a

| Reflux | Distillate | | | Tails or Bottoms | | | Dist. | % 143a |
|---|---|---|---|---|---|---|---|---|
| Flow (pph) | 143a (pph) | 12 (PPM) | Temp (C.) | 143a (pph) | 12 (pph) | Temp (C.) | 143a (WT %) | in Feed Recovered As Distillate Product |
| 40000 | 1000 | 100 | −27.4 | 0.07 | 4.93 | −6.7 | 1.3 | 100 |
| 30000 | 999 | 100 | −27.4 | 1.0 | 4.93 | −16.6 | 17.3 | 99.9 |
| 25000 | 994 | 100 | −27.4 | 5.8 | 4.93 | −22.8 | 53.9 | 99.4 |
| 20000 | 976 | 100 | −27.4 | 24 | 4.93 | −24.7 | 83.2 | 97.6 |
| 15000 | 851 | 100 | −27.4 | 149 | 4.94 | −25.2 | 96.8 | 85.1 |
| 10000 | 507 | 100 | −27.4 | 493 | 4.97 | −25.3 | 99.0 | 50.7 |

While the HFC-143 a product specification is met at all reflux rates, relatively high reflux rates are required. Large HFC-143a losses will result unless commercially prohibitive reflux flows are employed. Separating CFC-12 from HFC-143a is also made difficult due to a vapor-liquid equilibrium pinch point that forms at relatively low CFC-12 concentrations.

column base pressure 3 psi higher. The distillate temperature is about −27.4 degrees C., and the bottom column temperature varies from about 90.5 to 85.9 degrees C., depending of the extractant flow. Under these operating conditions, the HFC-143a product will leave in the distillate (overhead) stream from the column. The CFC-12 exits in the tails stream. Conditions are set so as to meet a composition of 100 parts per million (PPM) of CFC-12 in the HFC-143a distillate product, and the extractant feed rate is varied to show the effect on HFC-143a recovery.

The results of using this inventive extractive distillation process are shown below in Table 9.

TABLE 9

REMOVAL OF CFC-12 FROM HFC-143a

| Extr. | Reflx | Distillate | | | | Tails or Bottoms | | | % of 143a |
|---|---|---|---|---|---|---|---|---|---|
| Flow (pph) | Flow (pph) | 12 (PPM) | 143a (pph) | Extr (PPM) | Temp (C.) | 12 (pph) | 143a (pph) | Temp (C.) | in Feed Recovered as Distillate Product |
| 50000 | 5000 | 100 | 998 | 0.0 | −27.4 | 4.9 | 1.8 | 90.5 | 99.8 |
| 40000 | " | 100 | 997 | 0.0 | −27.4 | 4.9 | 2.9 | 90.4 | 99.7 |
| 30000 | " | 100 | 996 | 0.0 | −27.4 | 4.9 | 4.2 | 90.3 | 99.6 |
| 20000 | " | 100 | 991 | 0.0 | −27.4 | 4.9 | 8.7 | 90.1 | 99.1 |
| 15000 | " | 100 | 983 | 0.0 | −27.4 | 4.9 | 17 | 89.5 | 98.3 |
| 10000 | " | 100 | 946 | 0.0 | −27.4 | 4.9 | 54 | 85.9 | 94.6 |

High purity HFC-143a distillate is achieved at all extractant flows. By employing a sufficient methanol extractant, very high recoveries of HFC-143a can be achieved in contrast to the flow rate HFC-143a losses shown in Comparative Example 3.

COMPARATIVE EXAMPLE 4

In this Comparative Example, conventional distillation within a column with 62 stages is used for purifying a feed

EXAMPLE 3

In this Example of the invention, an extractive distillation column with 57 stages is used for purifying a feed stream with the same composition as in Comparative Example 4. The feed is introduced on stage 40 and the methanol extractant on stage 20, both at a temperature of −20 degrees C., with the column condenser pressure at 34.7 psia and the stream containing 1000 Lb./hr of HFC-143a with 5.025 Lb./hr of HFC-32 (5000 PPM by weight). The feed is introduced on stage 30 at a temperature of −20 degrees C., with the column condenser pressure at 34.7 psia and the column base pressure 3 psi higher. The distillate temperature varies from about −28.7 to −33.7 degrees C. depending on the distillate to feed ratio, and the bottom column temperature is about −25.3 degrees C. Conditions are set so as to meet a composition of 1 part per million (PPM) of HFC-32 in the HFC-143a tails product, and the distillate to feed ratio (based on HFC-143a in the feed) and reflux ratio are varied to meet the tails specification.

The results of using this conventional distillation method are below in Table 10.

extractant flow. Under these operating conditions, the HFC-143a product will leave in the distillate (overhead) stream from the column. The HFC-32 exits in the tails stream. Conditions are set so as to meet a composition of 100 parts per million (PPM) of HFC-32 in the HFC-143a distillate product, and the extractant feed rate and distillate to feed ratio (based on HFC-143a in the feed) are varied to show the effect on distillate product purity.

The results of using this inventive extractive distillation process are shown below in Table 11.

TABLE 10

REMOVAL OF HFC-32 FROM HFC-143a

| Reflux Ratio | Distillate | | | | Tails or Bottoms | | | Dist | % of 143a |
|---|---|---|---|---|---|---|---|---|---|
| | Flow (pph) | 143a (pph) | 32 (pph) | Temp (C.) | 143a (pph) | 32 (PPM) | Temp (C.) | 143a (WT %) | in Feed Recovered as Tails Product |
| 26 | 2484 | 92 | 5.0 | −28.7 | 908 | 1.0 | −25.3 | 94.8 | 90.8 |
| 55 | 2565 | 42 | 5.0 | −29.8 | 958 | 1.0 | −25.3 | 89.3 | 95.8 |
| 140 | 2375 | 12 | 5.0 | −32.2 | 988 | 1.0 | −25.3 | 70.3 | 98.8 |
| 188 | 2232 | 6.9 | 5.0 | −33.0 | 993 | 1.0 | −25.3 | 57.8 | 99.3 |
| 525 | 3627 | 1.9 | 5.0 | −33.7 | 998 | 1.0 | −25.3 | 27.3 | 99.8 |

While the goal of reducing the concentration of HFC-32 in the HFC-143a is satisfied, the recovery of HFC-143 a is reduced at lower reflux rations because an azeotropic or azeotrope-like composition is formed between HFC-143a and HFC-32 at these temperatures. However, this Example illustrates how these azetrope compositions can be used to remove HFC-32 from an HFC-143a containing mixture, e.g., thereby producing substantially pure HFC-143a exiting the column in the bottoms (tails) by reducing the concentration of HFC-32 in the first mixture.

TABLE 11

REMOVAL OF HFC-32 FROM HFC-143a

| Extr. Flow (pph) | Reflx Flow (pph) | Distillate | | | | Tails or Bottoms | | | % 143a |
|---|---|---|---|---|---|---|---|---|---|
| | | 32 (PPM) | 143a (pph) | Extr (PPM) | Temp (C.) | 32 (pph) | 143a (pph) | (C.) | in Feed Recovered As Distillate Product |
| 150000 | 5000 | 100 | 944 | 0.0 | −27.4 | 4.9 | 56 | 90.2 | 94.4 |
| 125000 | " | 100 | 933 | 0.0 | −27.4 | 4.9 | 67 | 90.0 | 93.3 |
| 100000 | " | 100 | 911 | 0.0 | −27.4 | 4.9 | 89 | 89.7 | 91.1 |
| 75000 | " | 100 | 835 | 0.0 | −27.4 | 4.9 | 165 | 88.7 | 83.5 |

EXAMPLE 4

In this example of the invention, an extractive distillation column with 57 stages is used for purifying a feed stream with the same composition as in Comparative Example 5. The feed is introduced on stage 40 and the methanol extractant on stage 20, both at a temperature of −20 degrees C., with the column condenser pressure at 34.7 psia and the column base pressure 3 psi higher. The distillate temperature is about −27.4 degrees C., and the bottom column temperature varies from 90.2 to 85.0 degrees C., depending upon the While the inventive process in this example shows little or no improvement versus the conventional process for separating HFC-32 from HFC-143a, nevertheless the use of the inventive process may be useful in separating HFC-32 from HFC-143a in cases when the HFC-143a contains other fluorocarbon impurities. For example, if a small amount of HFC-32 were present in the HFC-143a along with another impurity such as CFC-12, the HFC-32 and the CFC-12 would be removed together with the methanol extractant from the column tails. That is, if the inventive process is used to separate other impurities such as CFC-12 from HFC-143a, the concomitant removal of HFC-32 may be advantageous over the alternative of using a second distillation column employing conventional distillation to remove the HFC-32.

COMPARATIVE EXAMPLE 5

In this Comparative Example, conventional distillation within a column with 62 stages is used for purifying a feed stream containing 1000 Lb./hr of HFC-143a with 5.025 Lb./hr of HCFC-1113 (5000 PPM by weight). The feed is introduced on stage 30 at a temperature of −20 degrees C., with the column condenser pressure at 34.7 psia and the column base pressure 3 psi higher. The distillate temperature is about −27.4 degrees C., and the bottom column temperature varies from about −4.4 to about −25.2 degrees C., depending on the reflux flow. Conditions are set so as to meet a composition of 10 parts per million (PPM) of HCFC-1113 in the HFC-143a distillate product.

The results of using this conventional distillation method are shown below in Table 12.

TABLE 12

REMOVAL OF CFC-1113 FROM HFC-143a

| Reflux | Distillate | | | Tails or Bottoms | | | Dist | % 143a |
|---|---|---|---|---|---|---|---|---|
| Flow Ratio | 143a (pph) | 1113 (pph) | Temp (PPM) (C.) | 143a (pph) | 1113 (pph) | Temp (C.) | 143a (wt. %) | in Feed Recovered as Distillate Product |
| 5.0 | 5000 | 1000 | 10 −27.4 | <0.01 | 5.02 | −4.4 | <0.01 | 100 |
| 4.5 | 4500 | 1000 | 10 −27.4 | <0.01 | 5.02 | −4.4 | <0.01 | 100 |
| 4.4 | 4000 | 909 | 10 −27.4 | 91 | 5.02 | −25.0 | 94.8 | 90.9 |
| 4.4 | 3500 | 787 | 10 −27.4 | 213 | 5.02 | −25.1 | 97.7 | 78.7 |
| 4.5 | 3000 | 667 | 10 −27.4 | 333 | 5.02 | −25.2 | 98.5 | 66.7 |
| 4.6 | 2500 | 549 | 10 −27.4 | 451 | 5.02 | −25.2 | 98.9 | 54.9 |

While the HFC-143a product specification is met at all reflux rates, the HFC-143a losses in the tails become very high as the reflux rate is reduced.

EXAMPLE 5

In this Example of the invention, an extractive distillation column with 62 stages is used for purifying a feed stream with the same composition as in Comparative Example 5. The feed is introduced on stage 50 and the methanol extractant on stage 10, both at a temperature of −20 degrees C., with the column condenser pressure at 34.7 psia and the column base pressure 3 psi higher. The distillate temperature is about −27.4 degrees C., and the bottom column temperature varies from about 90.3 to about 89.0 degrees C., depending upon the extractant flow. Under these operating conditions, the HFC-143a product will leave in the distillate (overhead) stream from the column. The HCFC-1113 exits in the tails stream. Conditions are set so as to meet a composition of 10 parts per million (PPM) of HCFC-1113 in the HFC-143a distillate product, and the extractant flow rate is varied to show the effect on distillate product recovery.

The results of using this inventive extractive distillation process are shown below in Table 13.

TABLE 13

REMOVAL OF HCFC-1113 FROM HFC-143a

| Extr. Flow (pph) | Reflx Flow (pph) | Distillate | | | | Tails or Bottoms | | | % 143a in Feed Recovered As Distillate Product |
|---|---|---|---|---|---|---|---|---|---|
| | | 1113 (PPM) | 143a (pph) | Extr (PPM) | Temp (C.) | 1113 (pph) | 143a (pph) | Temp (C.) | |
| 60000 | 3000 | 10 | 989 | 0.0 | −27.4 | 5.02 | 11 | 90.3 | 98.9 |
| 55000 | "    | 10 | 987 | 0.0 | −27.4 | 5.02 | 13 | 90.3 | 98.7 |
| 50000 | "    | 10 | 985 | 0.0 | −27.4 | 5.02 | 15 | 90.2 | 98.5 |
| 45000 | "    | 10 | 981 | 0.0 | −27.4 | 5.02 | 19 | 90.1 | 98.1 |
| 40000 | "    | 10 | 976 | 0.0 | −27.4 | 5.02 | 24 | 90.0 | 97.6 |
| 35000 | "    | 10 | 967 | 0.0 | −27.4 | 5.02 | 33 | 89.7 | 96.7 |
| 30000 | "    | 10 | 946 | 0.0 | −27.4 | 5.02 | 54 | 89.0 | 94.6 |

HFC-143a (distillate) product quality goals are met at all extractant flows. Proper selection of the methanol extractant rate will result in low HFC-143a losses when removing the HCFC-1113. Methanol behaves as a conventional extractant when in the presence of HCFC-1113, i.e. the normally lower-boiling compound, (HFC-143a), goes overhead. This extractive distillation system can be used in conjunction with removing another impurity, e.g., CFC-12, where the methanol also functions as a conventional extractant.

EXAMPLE 6

In this example of the invention, an extractive distillation column with 57 stages is used for purifying a feed stream with a variety of impurities, containing 1000 Lb./hr of HFC-143a with 5.13 Lb./hr each of CFC-12, HCFC-133a, HFC-134a, HFC-143 and HFC-152a (5000 PPM by weight each). The feed is introduced on stage 40 and the methanol extractant on stage 20, both at a temperature of −20 degrees C., with the column condenser pressure at 34.7 psia and the column base pressure 3 psi higher. The distillate temperature is about −27.4 degrees C., and the bottom column temperature varies from about 90.4 to about 85.3 degrees C., depending of the extractant flow. Under these operating conditions, the HFC-143a product will leave in the distillate (overhead) stream from the column. The fluorocarbon impurities exit in the tails stream. Conditions are set so as to meet a composition of 100 parts per million (PPM) of total fluorocarbon impurities in the HFC-143a distillate product, and the extractant flow rate is varied to show the effect on distillate product recovery.

The results of using this inventive extractive distillation process are shown below in Table 14.

TABLE 14

REMOVAL OF CFC-12, HCFC-133a, HFC-134a, HFC-143 AND HFC-152a FROM HFC-143a

| Extr. Flow (pph) | Reflx Flow (pph) | Distillate Org (PPM) | 143a (pph) | Extr (PPM) | Temp (C.) | Tails or Bottoms Org (pph) | 143a (pph) | Temp (C.) | % 143a in Feed Recovered As Distillate Product |
|---|---|---|---|---|---|---|---|---|---|
| 50000 | 5000 | 100 | 998 | 0.0 | −27.4 | 25.5 | 1.9 | 90.4 | 99.8 |
| 40000 | " | 100 | 997 | 0.0 | −27.4 | 25.5 | 2.9 | 90.3 | 99.7 |
| 30000 | " | 100 | 996 | 0.0 | −27.4 | 25.5 | 4.3 | 90.2 | 99.6 |
| 20000 | " | 100 | 991 | 0.0 | −27.4 | 25.5 | 8.8 | 89.8 | 99.1 |
| 15000 | " | 100 | 980 | 0.0 | −27.4 | 25.5 | 20 | 89.0 | 98.0 |
| 10000 | " | 100 | 944 | 0.0 | −27.4 | 25.5 | 56 | 85.3 | 94.4 |

The HFC-143a product specification is met in all cases. The recovery of product is nearly quantitative at extractant flows above 20000 Lb./hr. The results are nearly identical to those in Example 4, wherein CFC-12 is the only impurity to be removed from the HFC-143 a. This example shows that additional impurities do not change the behavior of the CFC-12/HFC-143a/methanol extractive distillation system. While the additional impurities may also be removed readily by conventional distillation, if such are present along with a relatively difficult to remove impurity such as CFC-12, all of the impurities may conveniently be removed in the same extractive distillation system, i.e., thereby avoiding a distillation step.

EXAMPLE 7

The following examples demonstrate the existence of azeotropic and azeotrope-like compositions between binary pair mixtures consisting essentially of HFC-143a and CFC-115, HFC-143a and HFC-32, and HFC-143a and HFC-125.

To determine the relative volatility of each binary pair, the so-called PTx Method was used. In this procedure, for each binary pair, the total absolute pressure in a PTx cell of known volume was measured at a constant temperature for various known binary compositions. These measurements were then reduced to equilibrium vapor and liquid compositions in the cell using the NRTL equation. Samples of selected vapor and liquid sets were obtained and analyzed to verify their respective compositions.

The vapor pressure measured versus the composition in the PTx cell for the HFC-143a/CFC-115, HFC-143a/HFC-32 and HFC-143a/HFC-125 systems are shown in FIGS. 2 through 5, respectively. The experimental data points are shown in each Figure as solid points on each Figure and the curve is drawn by using computer modeling.

Figure 2:
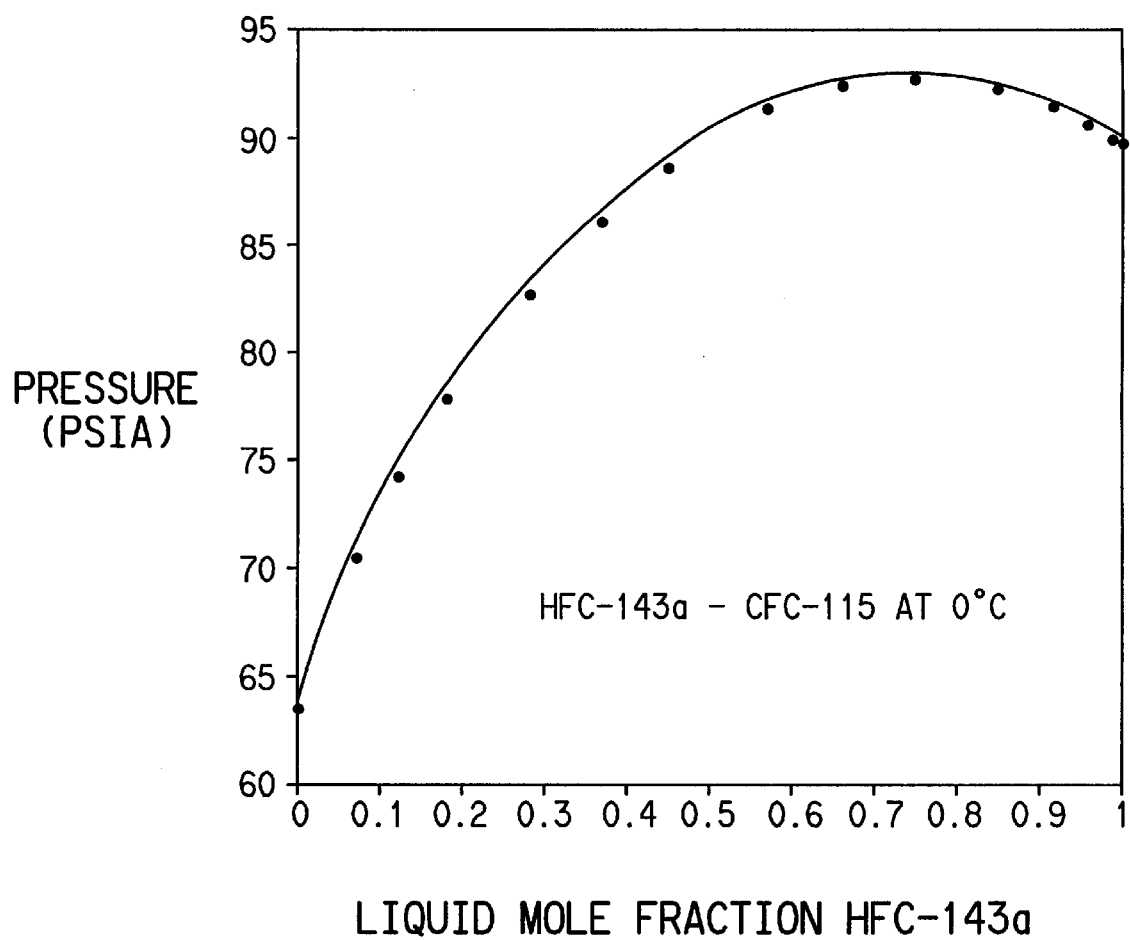
FIG. 2—FIG. 2 is a graphical representation of an azeotropic or azeotrope-like composition consisting essentially of HPC-143a and CFC-115 at a temperature of about 0 degrees C.

Referring now to FIG. 2, FIG. 2 illustrates graphically the formation of an azeotropic and azeotrope-like composition consisting essentially of HFC-143a and CFC-115 at 0 degrees C., as indicated by a mixture of about 75.6 mole % HFC-143a and 24.4 mole % CFC-115 having the highest pressure over the range of compositions at this temperature. Based upon these findings, it has been calculated that an azeotropic or azeotrope-like composition of about 73.3 mole % HFC-143a and 26.7 mole % CFC-115 is formed at −65 degrees C. and 6.1 psia and an azeotropic or azeotrope-like composition of about 90.8 mole % HFC-143a and about 9.2 mole % CFC-115 is formed at 70 degrees C. and 515 psia. Accordingly, the present invention provides an azeotropic or azeotrope-like composition consisting essentially of from about 73 to about 91 mole % HFC-143a and from about 27 to about 9 mole % CFC-115, said composition having a boiling point of from about 6 psia at −65 degrees C. to about 515 psia at 70 degrees C.

Figure 3:
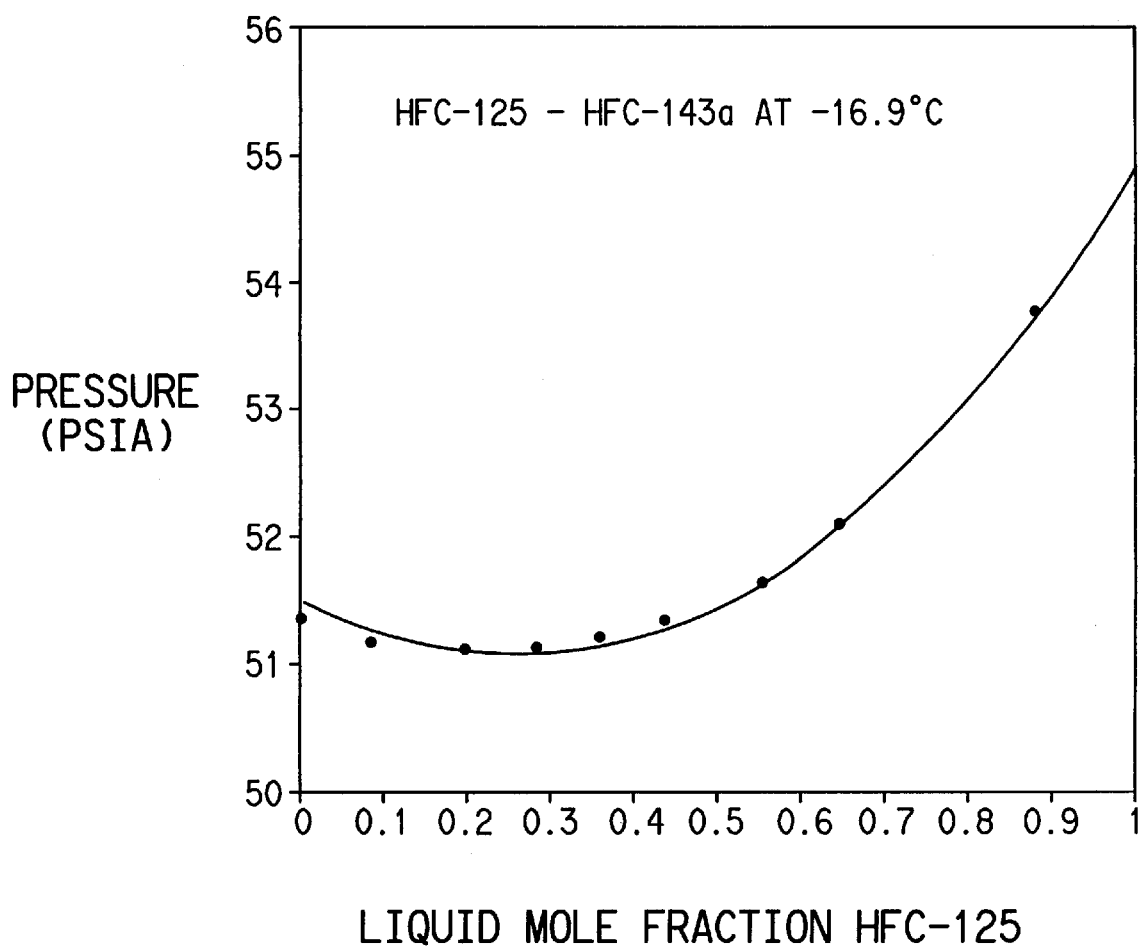
FIG. 3—FIG. 3 is a graphical representation of an azeotropic or azeotrope-like composition consisting essentially of HFC-143a and HFC-125 at a temperature of about −16.9 degrees C.

Referring now to FIG. 3, FIG. 3 illustrates graphically the formation of an azeotropic and azeotrope-like composition consisting essentially of HFC-125 and HFC-143a at −16.9 degrees C., as indicated by a mixture of about 27.2 mole % HFC-125 and 72.8 mole % HFC-143a having the lowest pressure over the range of compositions at this temperature. Based upon these findings, it has been calculated that an azeotropic or azeotrope-like composition of about 41.1 mole % HFC-125 and 58.9 mole % HFC-143a is formed at −50 degrees C. and 12.5 psia and an azeotropic or azeotrope-like composition of about 5.2 mole % HFC-125 and about 94.8 mole % HFC-143a is formed at 10 degrees C. and 122.1 psia. Accordingly, the present invention provides an azeotropic or azeotrope-like composition consisting essentially of from about 5 to about 41 mole % HFC-125 and from about 95 to 59 mole % HFC-143a, said composition having a boiling point of from about −50 degrees C. at 12 psia to about 10 C. at 122 psia.

Figure 4:
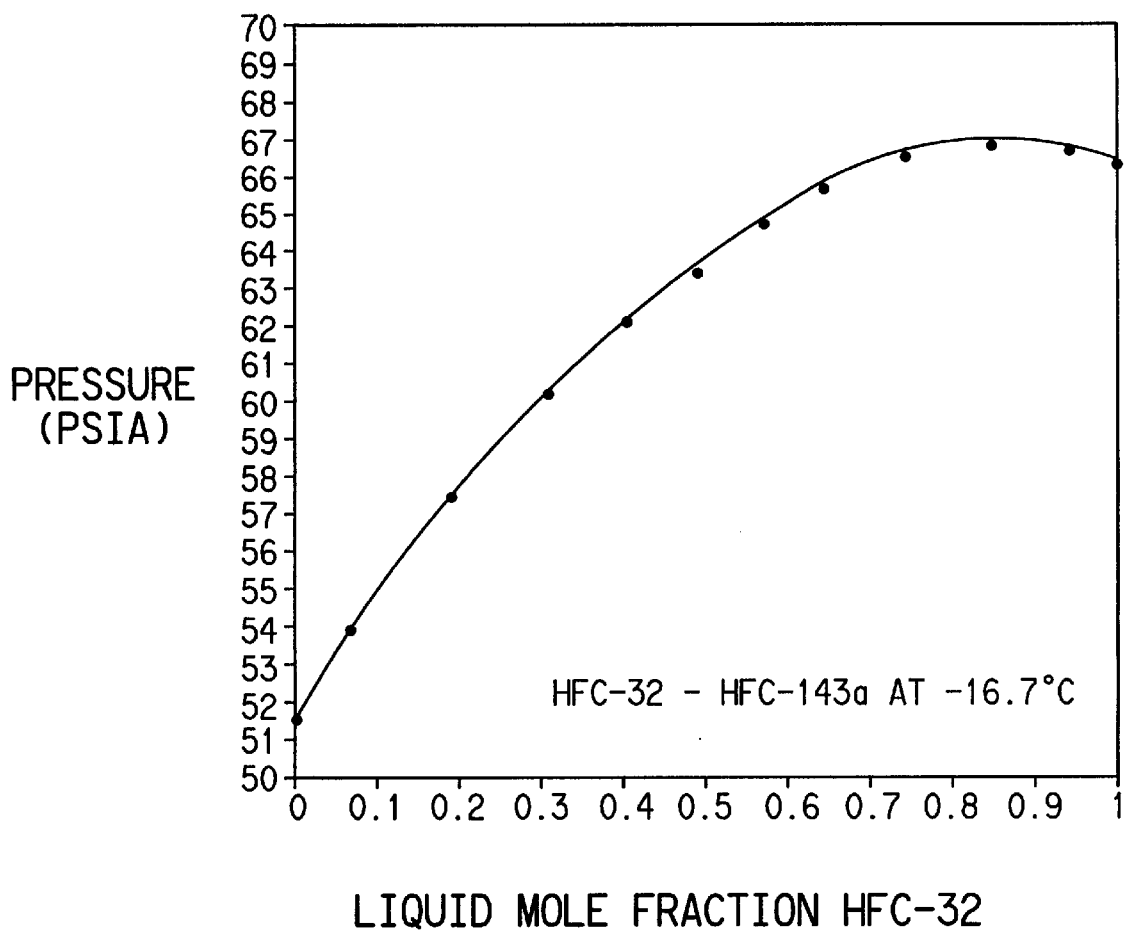
FIG. 4—FIG. 4 is a graphical representation of an azeotropic or azeotrope-like composition consisting essentially of HFC-143a and HFC-32 at a temperature of about −16.7 degrees C.

Referring now to FIG. 4, FIG. 4 illustrates graphically the formation of an azeotropic and azeotrope-like composition consisting essentially of HFC-143a and BFC-32 at −16.7 degrees C., as indicated by a mixture of about 12.0 mole % HFC-143a and 88.0 mole % HFC-32 having the highest pressure over the range of compositions at this temperature. Based upon these findings, it has been calculated that an azeotropic or azeotrope-like composition of about 28.3 mole % HFC-143a and 71.7 mole % HFC-32 is formed at −80 degrees C. and 2.9 psia and an azeotropic or azeotrope-like composition of about 0.2 mole % HFC-143a and about 99.8 mole % HFC-32 is formed at 24 degrees C. and 239 psia. Accordingly, the present invention provides an azeotropic or azeotrope-like composition consisting essentially of from about 0.2 to about 28 mole % HFC-143a and from about 99.8 to 12 mole % HFC-32, said composition having a boiling point of from about −80 degrees C. at 2.9 psia to about 24 degrees C. at 239 psia.

Figure 5:
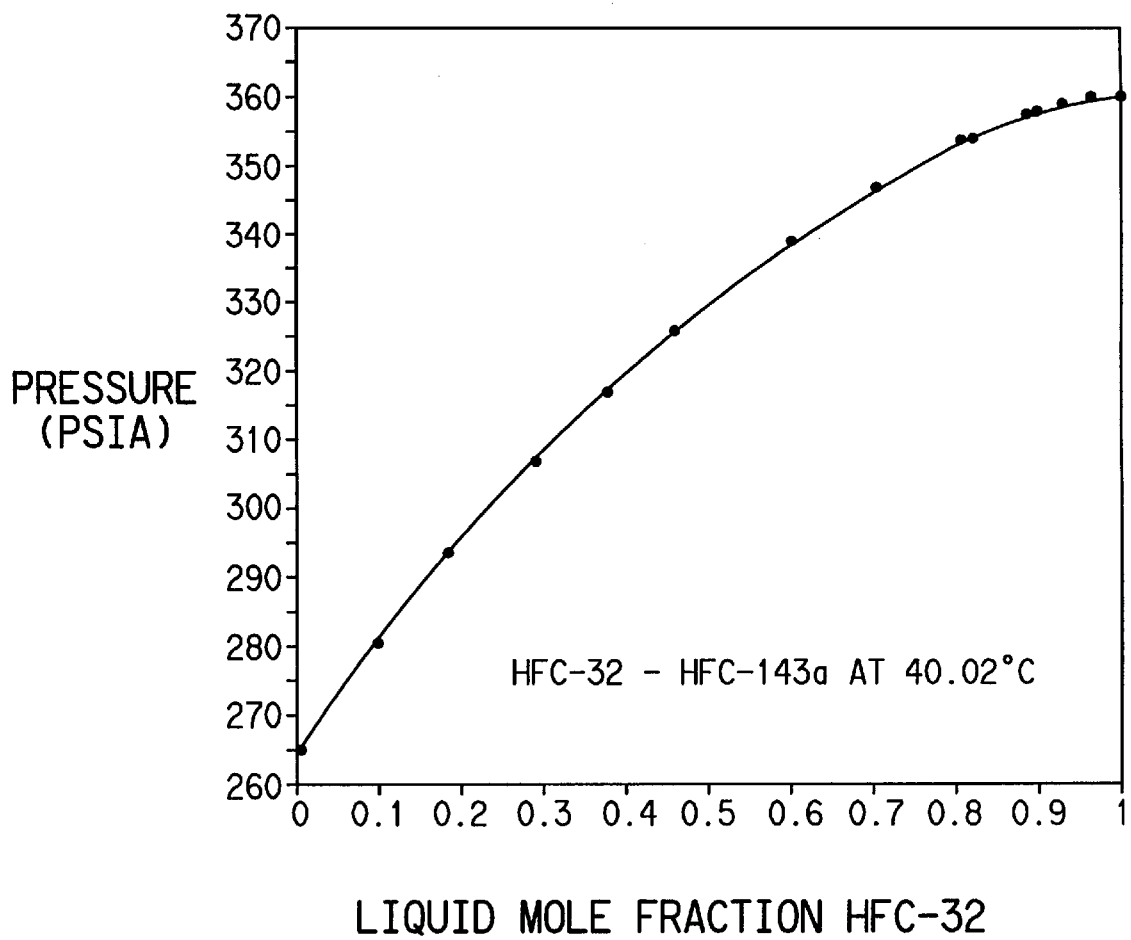
FIG. 5—FIG. 5 is a graphical representation of the results from PTx measurements on HFC-143a and HFC-32 mixtures at a temperature of about 40 degrees C.

Referring now to FIG. 5, FIG. 5 shows the absence of an azeotropic or azeotrope-like composition for HFC-143a/HFC-32 mixtures at a temperature of about 40 degrees C. since no mixture of these two compounds possesses a greater or lessor vapor pressure than either of the pure compounds. Based upon vapor pressure data at 40 and −16.7 degrees C., it has been calculated that azeotropic or azeotrope-like concentration cease to exit above about 25 degrees C. Based upon these data, removing HFC-32 from HFC-143a may be facilitated by operating a distillation column with a condenser temperature above about 25 degrees.

While certain aspects of the invention have been described in particular detail, a person in this art would understand that other embodiments and variations are covered by the appended claims.

The following is claimed:

1. A process for separating 1,1,1-trifluoroethane from a first mixture comprising 1,1,1-trifluoroethane and at least one member from the group consisting of pentafluoroethane, dichlorodifluormethane, chlorotrifluoroethylene and difluoromethane, comprising the following steps:

1. adding said first mixture to a vessel, said mixture comprising 1,1,1-trifluoroethane and at least one member from said group containing an excess of 1,1,1-trifluoroethane over the effective amount of 1,1,1-trifluoroethane necessary to form a substantially constant boiling composition with said at least one member;

2. heating said mixture to a temperature at which said substantially constant boiling composition distills from said mixture; and 3. recovering a second mixture of the excess 1,1,1-trifluoroethane remaining in said vessel.

2. The process of claim 1 in which said first mixture further comprises at least one impurity selected from the group consisting of chlorodifluoromethane difluoromethane, 1,1,2-trifluoroethane, 2-chloro-1,1,1-trifluoroethane, 1,1,1,2-tetrafluoroethane, 1-chloro-1,1-difluoroethane, 1,1-difluoroethane wherein said impurity remains in said second mixture after distillation of said substantially constant boiling composition, comprising the further step of heating said second mixture to separate said impurity from 1,1,1-trifluorethane to yield substantially pure 1,1,1-trifluoroethane.

3. The process of claim 1 wherein said first mixture comprises a substantially constant boiling composition consisting essentially of about 73 to about 91 mole % HFC-143a and from about 9 to about 27 mole % CFC-115 at a temperature of about −65 to about 70 degrees C. and a vapor pressure of about 6.1 to about 515 psia.

4. The process of claim 1 wherein said first mixture comprises a substantially constant boiling composition consisting essentially of about 0.2 to about 28 mole % 1,1,1-trifluoroethane and about 99.8 to 12 mole % difluoromethane.

5. The process of claim 1 wherein said first mixture comprises a substantially constant boiling composition consisting essentially of about 5 to 41 mole % pentafluoroethane and about 95 to 59 mole % 1,1,1-trifluoroethane.

* * * * *